United States Patent [19]
Ek

[11] Patent Number: 5,741,710
[45] Date of Patent: Apr. 21, 1998

[54] REACTION CHAMBER AND A METHOD FOR GENERATING A GASEOUS SAMPLE BASED ON THE USE THEREOF

[76] Inventor: Paul Ek, Helastentie 168, FIN-21330 Paattinen, Finland

[21] Appl. No.: 663,046
[22] PCT Filed: Dec. 15, 1994
[86] PCT No.: PCT/FI94/00565
  § 371 Date: Jun. 11, 1996
  § 102(e) Date: Jun. 11, 1996
[87] PCT Pub. No.: WO95/17964
  PCT Pub. Date: Jul. 6, 1995

[30] Foreign Application Priority Data

Dec. 31, 1993 [FI] Finland ............... 935952

[51] Int. Cl.⁶ ............ G01N 33/20; G01N 21/71; B01L 3/00
[52] U.S. Cl. ............ 436/73; 436/81; 436/171; 436/181; 436/182; 436/183; 422/50; 422/68.1; 422/99; 417/442; 417/503; 417/545; 417/547
[58] Field of Search ............ 417/442, 443, 417/444, 502, 503, 545, 547, 569, 571; 422/50, 68.1, 99; 436/73, 81, 171, 181, 182, 183

[56] References Cited

U.S. PATENT DOCUMENTS

| | | | |
|---|---|---|---|
| 3,514,210 | 5/1970 | Hrdina | 417/503 X |
| 4,118,152 | 10/1978 | Bron | 417/545 X |
| 4,230,665 | 10/1980 | Huber | 436/182 X |
| 4,268,478 | 5/1981 | Huber | 422/82.09 |
| 4,740,356 | 4/1988 | Huber | 422/81 |
| 4,837,374 | 6/1989 | Brown et al. | 422/130 |
| 4,906,580 | 3/1990 | Meserole | 436/181 X |

FOREIGN PATENT DOCUMENTS 55-13840  1/1980  Japan.

OTHER PUBLICATIONS

J.C. Van Loon et al. *Anal. Lett.* 1974, 7, 505–513.
R.G. Smith et al. *Anal. Chim. Acta* 1977, 93, 61–67.
R. Robert et al. *Rep—Natl. Inst. Metall. (S. Afr.)* 1979, 2023.
C.J. Pickford *Anal. Chim Acta.* 1981, 106, 464–467.
C.J. Peacock et al. *Anal. Chim. Acta.* 1981, 106, 931–938.
R. Kobayashi et al. *Bunseki Kagaku* 1982, 31, 467–469.
M. Uemoto *Kogyo Yosui* 1992, 409, 83–87.
P. Ek et al. *J. Anal. At. Spectrom.* 1995, 10, 121–126.

*Primary Examiner*—Arlen Soderquist
*Attorney, Agent, or Firm*—Adduci, Mastriani & Schaumberg, L.L.P.

[57] ABSTRACT

The invention relates to a reaction chamber, which includes a cylindrical vessel, with at one end, at least one inlet or outlet tube or lead-through fitted with a valve for a liquid or gaseous component. The other end of the vessel is open. The reaction chamber further comprises a plunger, which performs a reciprocating movement within the cylindrical vessel in axial direction through the open end of the vessel. The plunger tightens against the inner wall of the cylindrical vessel, and has at least one channel, in substantially axial direction, fitted with a valve or connected to a tube fitted with a valve. The invention relates also to an assay method based on the use of the reaction chamber.

10 Claims, 4 Drawing Sheets

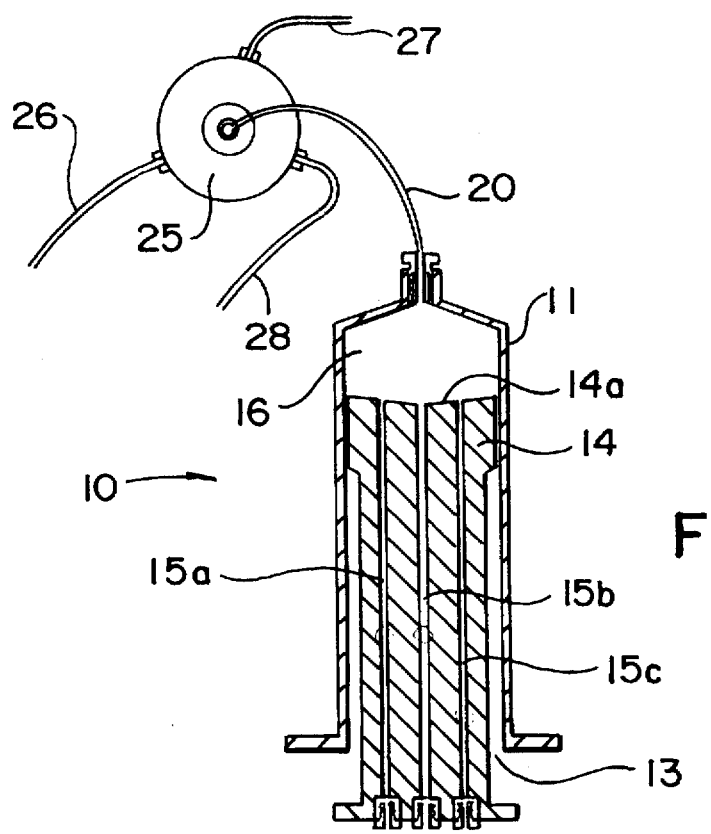
Fig_2
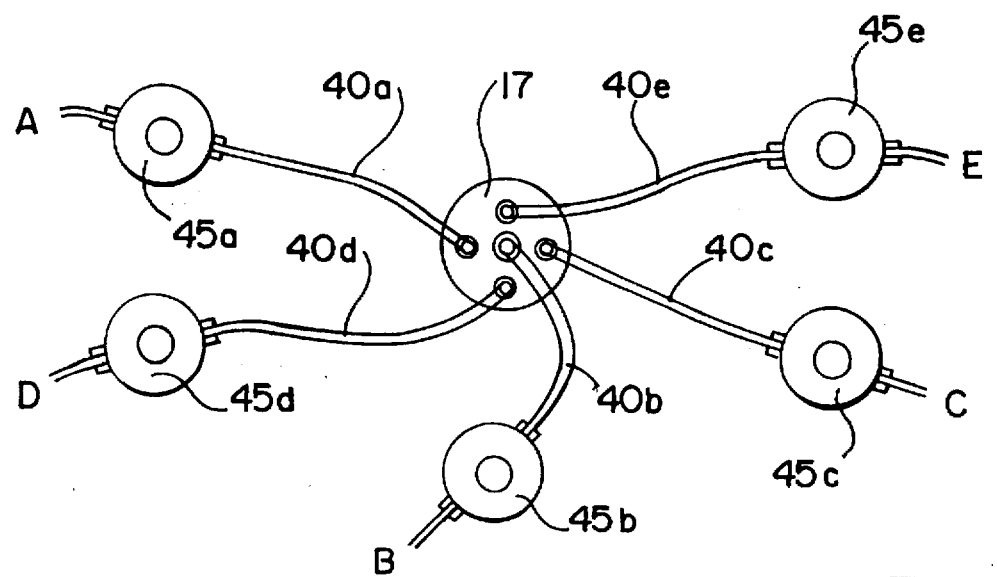
Fig_3

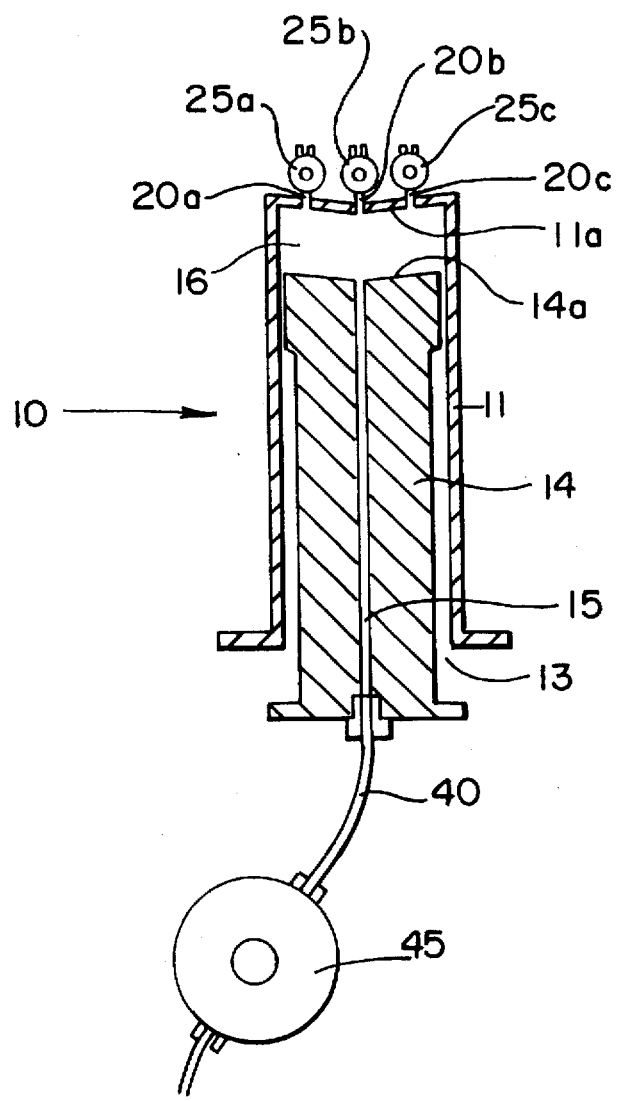
Fig_4

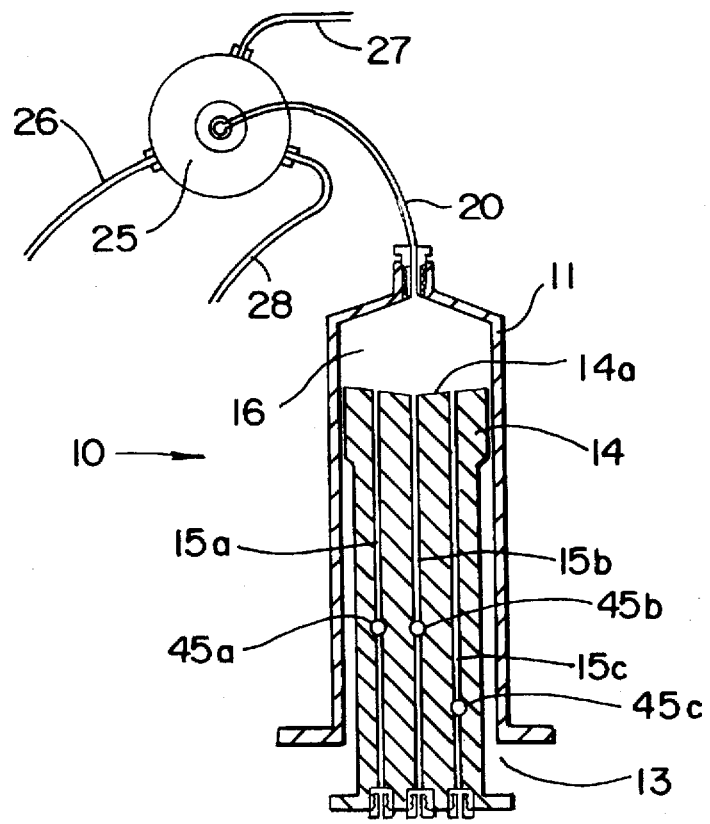
Fig_5

REACTION CHAMBER AND A METHOD FOR GENERATING A GASEOUS SAMPLE BASED ON THE USE THEREOF

BACKGROUND OF THE INVENTION

The invention relates to a novel reaction chamber particularly for analytical use. The invention relates also to a novel assay method based on the use of the said reaction chamber.

For the quantitative assay of a component in a sample a reaction chamber is used into which the sample and one or more reactants, usually in liquid or gaseous state, are introduced. The component to be assayed is reacted in the reaction chamber with the reactant(s), and one or, usually, several reaction products are formed in liquid or gaseous state. One of the reaction products is representative of the component to be assayed and shall be quantitated with a suitable detector. In certain cases the entire reaction mixture can be introduced into the detector, which records the component to be assayed. In most cases, however, the component to be assayed has to be separated from the reaction mixture before feeding it into the detector for measurement, because other reaction products may interfere with the accuracy of the quantitation of the component to be assayed or load the detector unnecessarily. Especially in those situations in which the component to be assayed is in gaseous state while the other reaction products are liquid it is important that the liquid components be separated from the gaseous component to be assayed, as liquids interfere with the functioning of instruments for the detection of gases.

Modern analytical instruments are required to offer, in addition to high accuracy, also high throughput, i.e. they must be capable of performing a great number of analyses per unit time. Rapid emptying of the reaction vessel is also important to save time. Emptying must also be as complete as possible in order to avoid contamination of fresh samples and reactants.

Reaction chambers for analytical use are nowadays usually vessels having a specified volume, said vessels being emptied and possibly cleansed after the completion of the reaction, before being refilled with a new sample and reactant for the next determination. Complete emptying is difficult especially when the component to be assayed is in gaseous state. The gas to be assayed is usually displaced form the reaction vessel by means of an inert gas, which then, as a carrier gas, carries the gaseous analyte into the detector. This type of reaction was described e.g. by H äyrynen H et al., Atomic Spectroscopy, Vol. 6, No. 4, pp. 88–90 (1985). This manner of emptying is, however, fraught with several difficulties. The carrier gas mixes rather completely with the gas to be determined, which means that complete removal of the analyte gas from the reaction vessel takes a long time. The analyte gas to be introduced into the detector will be considerably diluted, which contributes to the reduction of the accuracy of the assay. In addition, other reaction products, which are usually in liquid state, are carried with the gas stream as droplets, and will load the detector.

SUMMARY OF THE INVENTION

The objective of this invention is to resolve and remove the problem described above and to design a novel reaction chamber, from which reaction products can be rapidly removed, and which can be rapidly refilled with new sample and reactants. The analyte in the reaction mixture can also be efficiently separated from other reaction products whenever the analyte is distributed in a phase separate from the one in which the other reaction products are found.

The invention thus relates to a reaction chamber comprising a cylindrical vessel having in one end at least one inlet or outlet tube or a lead-through fitted with a valve, for the liquid or gaseous component. The invention is characterized by the other end of the cylindrical vessel being open and by the reaction chamber further comprising a plunger performing a reciprocating movement within the cylindrical vessel in axial direction through the open end of the vessel. The invention is further characterized by the plunger sealing against the inner wall of the cylindrical vessel and having at least one substantially axially directed channel fitted with a valve or connected to a tubing fitted with a valve.

The invention relates also to a quantitative assay method for an element generating a gas or a gaseous hydride, in which method a sample containing the element together with sodium borohydride and an acid is fed into the reaction chamber and reacted. The gas mixture evolved in the reaction is displaced from the reaction chamber and fed into a plasma spectrometer for the quantitation of the element. The method is characterized by performing the reaction in a reaction chamber, into which chamber the sample, sodium borohydride and acid are introduced by aspiration or pumping by driving the plunger outwards in the vessel, and from which chamber the gas mixture evolved in the reaction is displaced by driving the plunger inwards in the vessel. Finally liquid reaction products are removed from the reaction chamber by further continuing the inward movement of the plunger.

According to one embodiment the inlet or outlet tube is connected to a multi-channel valve which is used to feed the sample and one or more reagents successively into the reaction chamber.

According to another embodiment the plunger has several channels, substantially in axial direction, which are connected to a tube fitted with a valve.

According to a third embodiment several tubes or lead-throughs fitted with a valve are fixed in one end of the vessel.

BRIEF DESCRIPTION OF THE DRAWINGS

The invention will be illustrated by reference to the appended drawings, in which FIG. 2 shows the reaction chamber in axial cross-section according to another embodiment FIG. 3 shows the bottom of the plunger of the reaction chamber of FIG. 2 and the tubes with associated valves connected to the channels of the plunger FIG. 4 shows the reaction chamber in axial cross-section according to a third embodiment FIG. 5 shows the reaction chamber in axial cross-section according to another embodiment.

DETAILED DESCRIPTION OF THE PREFERRED EMBODIMENTS

Figure 1:
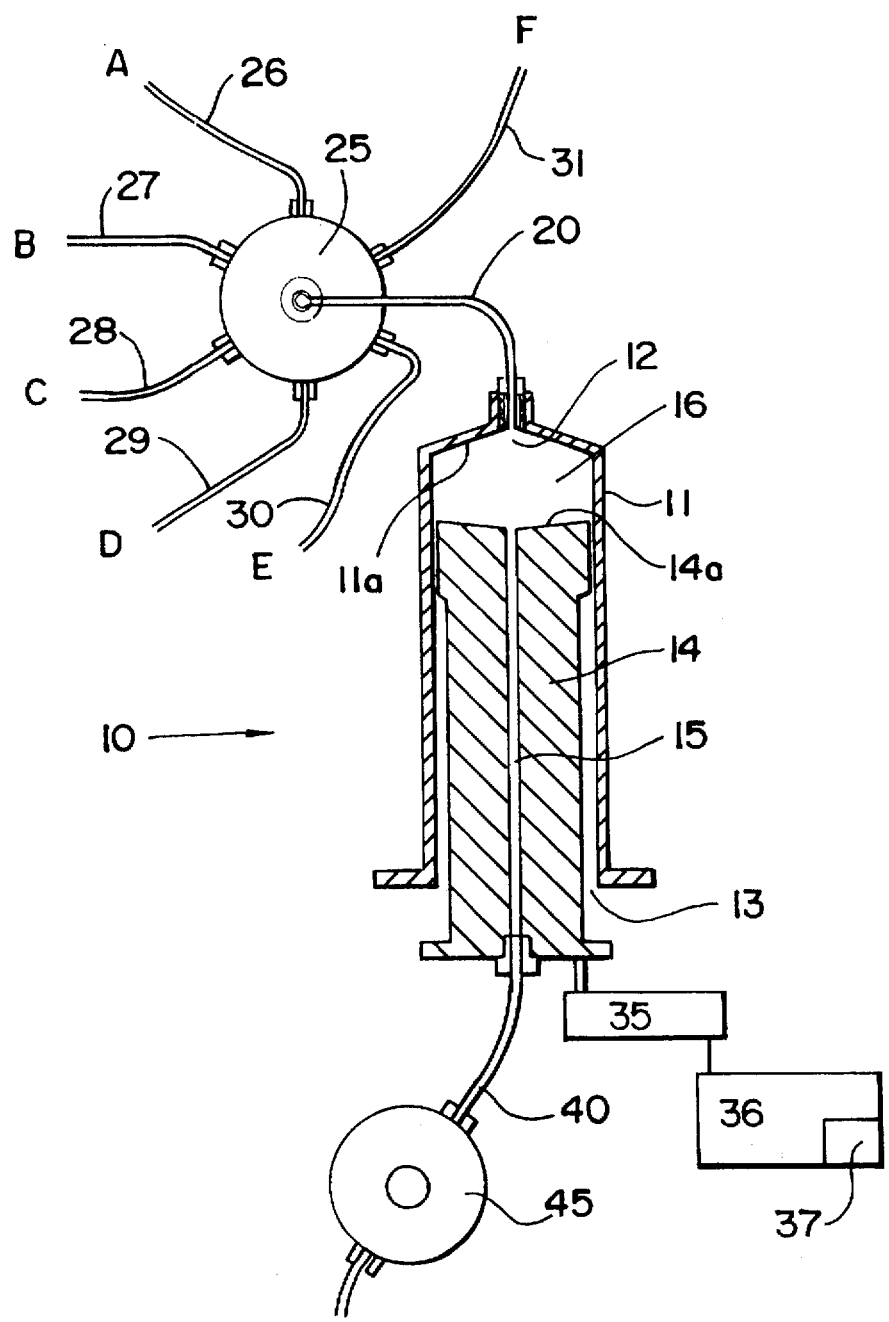
FIG. 1 shows the reaction chamber in axial cross-section

FIG. 1 shows the reaction chamber 10 in cross-section. The reaction chamber comprises a cylindrical vessel 11, having at one end 12 an inlet or outlet tube 20, fitted with a valve 25, for the gaseous or liquid component. The other end 13 of the vessel 11 is open. The plunger 14 can be driven inside the cylindrical vessel 11 in axial direction in a reciprocating movement, through the open end 13. The plunger tightens against the inner wall of the cylindrical vessel. Channel 15 runs through the plunger substantially in direction of the axis of the plunger. Channel 15 is connected to tube 40 fitted with valve 45. Alternatively valve 45 could be located directly in channel 15 inside the plunger. In the embodiment of FIG. 1 valve 25 associated with inlet or outlet tube 20 is a multi-channel valve. The multi-channel valve 25 can be used to feed sample A and one or more reagents B, C, D, E, F one after another into the reaction chamber through tubes 26–31.

The operation of the reaction chamber according to FIG. 1 can be described as follows. Valve 45 is closed and the plunger 14 is forced outwards in relation to the vessel 11 by means of a suitable drive mechanism, e.g. an electric motor or a pneumatic cylinder. Vacuum is generated in the space 16 between plunger 14 and vessel 11. By opening successively the multi-channel valve 25 to inlet tubes 26, 27, 28 . . . the components A, B, C . . . can be fed into the reaction chamber. If a gas is evolved in the reaction the plunger is driven outwards from the vessel during the reaction. If the analyte is a gaseous component evolved in the reaction valve 25 can be opened after the reaction is completed and the gaseous analyte can be channeled to the measuring detector through said valve. The gaseous component is displaced from the chamber by driving the plunger inwards in vessel 11. After the gas has been removed completely valve 25 is closed and valve 45 opened. By driving the plunger further inwards in vessel 11 unreacted components and the liquid components (so-called wastes) formed in the reaction can be removed.

It can be seen in FIG. 1 that the end 14a of the plunger 14 which enters the vessel 11 is slightly funnel-shaped. When the reaction chamber is operated in vertical position like in the figure the removal of liquid compounds is facilitated by this shape. Another advantage is that a certain space is still left between the end 14a of the plunger and the end 11a of the vessel 11 when the plunger has been pushed all the way into the vessel 11. This allows the use of a magnetic mixer in the reaction space 16, which is useful in many reactions in order to achieve complete mixing of the sample and the reagents. The magnetic mixer conforms to the reciprocating movement of the plunger.

FIG. 2 shows another embodiment of the reaction chamber in longitudinal cross-section. Several channels 15a, 15b, 15c etc. run through the plunger. FIG. 3 shows the bottom 17 of the plunger of the reaction chamber of FIG. 2. The tubes 40a, 40b, 40c . . . fitted with valves 45a, 45b, 45c . . . have been connected to the channels 15a, 15b, 15c etc. ending in the bottom 17. The end 14a of the plunger is again slightly funnel-shaped.

The embodiment according to FIG. 2 allows the simultaneous introduction of several compounds into the reaction chamber. The sample A and the reagents C–E can be introduced simultaneously through tubes 40a respectively 40c–40 e by driving the plunger 14 outwards from the vessel 11 while maintaining the valves 45a respectively 45c–45e open and the valves 25 and 45b closed. If less compounds are required to be introduced as to take all the tubes 40c–e, the valves 45 of the tubes not in use will be closed. Tube 40b and its valve 45b are reserved for the removal of liquid compounds (wastes). After the introduction of the compounds all valves 45 are closed. After the completion of the reaction the gaseous analyte is removed through tube 20 by opening the valve 25 and driving the plunger inwards in the vessel 11. After the removal of the gas valve 25 is closed while valves 45a and 45c–e are still kept closed. By opening valve 45b and driving the plunger further inwards in the vessel 11 liquid reaction products and unreacted compounds are emptied from the reaction chamber.

In the designs of FIG. 2 and 3 the valves 45 have been connected to tubes 40 outside the plunger. This arrangement has the disadvantage of leaving a rather large dead volume in tubes 40 and channels 15. To avoid this, the valves 45a–c may be alternatively located inside the plunger directly in the channels 15, as shown in FIG. 5.

The sample and reagents can be introduced by aspiration or by pumping them into the reaction chamber. Pumping is the preferred alternative, if high accuracy of feeding is required.

The designs of FIGS. 2 and 3 have the further advantage, in addition to the rapid introduction of compounds, of reserving the tube 20 entirely for the transport of the gaseous component. The risk of contamination by liquid components is then avoided.

To eliminate contamination, the reaction chamber can also be rinsed with e.g. argon gas or distilled water after emptying and before refilling. The purge with argon gas can be performed e.g. in the following way: The plunger is retracted outwards while valve 25 is kept open towards the inlet tube of argon, and other valves are shut. Then the vessel is emptied via valve 45b by driving the plunger inwards in the vessel 11 while the other valves are shut. If distilled water is used for rinsing, one of the channels connected to valve 25 must be reserved for the inlet of distilled water.

FIG. 4 shows an alternative reaction chamber, in which the sample and reagents can be fed simultaneously through tubes 20a–c fitted with valves 25a–c located at the end 11a of vessel 11. In this figure the end 11a has been shaped to conform to the funnel-like end of plunger 14a when the plunger is completely driven inside the vessel 11. This shape is advantageous for a complete emptying.

The reaction chamber comprises preferably also a drive mechanism 35 to move the plunger 14 and a control unit 36 comprising all components necessary for the control of the drive mechanism and the valves. The control unit comprises preferably also a processor 37 to control the drive mechanism and the valves.

The reaction chamber described above is particularly well suited to situations in which gaseous reaction products are formed, because handling of such reaction mixtures is particularly difficult, and no useful designs are available for the separation of the gas and liquid phases. The reaction chamber according to the invention is also applicable to reactions in which no gaseous but, instead only liquid reaction products are formed. The rapid addition of sample and reagents into the reaction chamber and the rapid and complete removal of reaction products are characteristics which make the reaction chamber according to the invention considerably superior to devices of prior art.

The use of a reaction chamber according to this invention is, of course, not limited to situations in which a chemical reaction between the different components takes place. It is applicable as well to different physical unitary operations such as absorption, extraction and mixing. Extraction, like a reaction producing gaseous reaction products, is a two-phase system with one phase being considerably lighter than the other phase. The operational schemes of extraction and gas treatment are thus largely comparable. When the reaction chamber is used in absorption processes, e.g. when components in a gas phase are to be transferred into a liquid phase, this reaction chamber can be used to transfer analytes easily into the medium most suitable for the detection method.

In the claims on the reaction chamber, to be presented in the following section, the work "reaction" shall be interpreted as covering both chemical reactions and physical binding processes.

In two-phase treatments like gas-forming reactions and extraction it is preferable to use the reaction chamber in a vertical position. In other kinds of reactions the reaction chamber may be used in any position.

The reaction chamber according to the invention has enabled a new type of quantitative assay method for elements which become gaseous under the effect of sodium borohydride, e.g. for those which are able to form a gaseous hydride in acidic conditions under the effect of sodium borohydride. Elements forming hydrides are typically bismuth, germanium, selenium, antimony, arsenic, lead, tin and tellurium.

According to a known method these elements are usually assayed by dispersing pneumatically a liquid sample containing the element to be determined to form an aerosol, which is then introduced into the plasma of a spectrometer, in which the elements contained in the sample are atomized, excited and ionized. This method is useful in the determination of high concentrations of elements, but it is far too inaccurate in the determination of low element concentrations. The reason for this is that only 1% of the element in the sample is recovered from the nozzle of the nebulizer while 99% is lost from the system through other routes. Only part of the amount delivered from the nozzle of the nebulizer reaches the excitement region of the plasma. To remedy this, a continuous process has been developed (Ek, P & Hulden, S-G, Talanta, Vol. 34, No. 5, pp. 495–502 1987), in which the elements are reacted with sodium borohydride in acidic solution to produce a gaseous hydride. The accumulated hydride gas is removed in a continuous process from the reactor by means of an inert carrier gas and carried into a plasma spectrometer used as a detector. This method has, however, some disadvantages, e.g. high consumption of reagents and inferior stability when the gas is fed into the plasma.

The method according to the invention is also suitable for the determination of mercury. Mercury, however, does not produce a hydride; instead, it becomes itself gaseous under the effect of sodium borohydride. Mercury can be determined with the same reagents used in the reactions to form a hydride. Sodium borohydride is known to reduce Hg(I) and Hg(II) ions to metallic Hg(O), which is gaseous already at room temperature. After the reduction gaseous mercury can be introduced, like gaseous hydrides, e.g. by means of a capillary column, in the middle of the plasma, and the emission signal can be measured spectrometrically.

In the method according to the invention the sample containing the element to be determined and the reagent solutions (5M HCl and 1% $NaBH_4$) are introduced into the reaction chamber either successively from the above, according to FIG. 1, or simultaneously according to FIG. 2 or FIG. 4, respectively, through the channels 15 of the plunger of the reaction chamber or, respectively, the tubes 20 fixed at the end 11a of the vessel. In this reaction the element (mercury) becomes gaseous or a gaseous hydride of the element and hydrogen gas are produced. The gaseous mixture is displaced from the reaction chamber after the completion of the reaction by one of the methods described above. The entire gaseous mixture, into which the element to be determined has been transferred completely, is fed into the middle of the plasma of the spectrometer. After the gas mixture has been removed from the reaction chamber, liquid waste is also removed by one of the methods described above. Especially good results are obtained by feeding the gas in the middle of the plasma by means of a quartz capillary tube.

In the reaction described above, in which sodium borohydride is used, it is advantageous to employ the reaction chamber of FIG. 2, into which the components are introduced from below. In this way an excessively strong surface reaction of sodium borohydride is avoided.

The invention relates also to a method for introducing samples in the middle of the plasma in DCP (Direct Current Plasma) or ICP (Inductively Coupled Plasma) atomic emission spectrometers or in ICP-MS (Inductively Coupled Plasma) mass spectrometer. The method is based on replacing the conventional sample introduction system (pneumatic nebulizer) of the spectrometer with a thin capillary tube (inner diameter 0.1 to 0.5 mm), through which the gaseous or liquid sample to be analyzed or a mixture containing the sample is forced by pressure. The capillary tube is preferably of quartz. Due to the high melting point of quartz the tip of the capillary can be taken quite close to the excitation zone of the plasma. Decomposition of the gas or liquid is avoided and it can be centered within a very narrow zone in the middle of the plasma. If the component to be analyzed is liquid the thermal energy of the plasma (T=5000K) can be exploited to vaporize the liquid at the tip of the capillary. The vaporized liquid is forced by pressure in the middle of the plasma, in which the elements contained in the sample are excited. Because the inner diameter of the capillary tube is small the dead volume in the tube is also very small. For a length of 50 cm of the capillary tube and a diameter of 0.1 mm, the dead volume is only 3.9 µl. This allows the use of extremely small sample volumes, and in practice a volume of 10–50 µl is sufficient. It may be mentioned for comparison that conventional techniques usually require 2–5 ml. This method of sample introduction also guarantees efficient use of the sample, since it allows the introduction of 100% of the elements of the sample in the middle of the excitation zone of the plasma.

By combining the reaction chamber according to the invention with the capillary tube introduction method e.g. metals present in an aqueous phase can be analyzed with high precision in the following way: An extraction is performed in the reaction chamber, in which the metal complexes or compounds are extracted from the heavy aqueous phase into the lighter phase, which consists of a suitable organic solvent. The metal concentration of the organic phase can be determined by displacing the organic phase from the reaction chamber and feeding it into the plasma of a spectrometer through a thin quartz capillary tube. The thermal radiation (T=5000K) of the plasma vaporizes the organic phase at the tip of the tube, the metal complex is taken into the plasma and the metal is excited. The emission of metal ions is measured with the spectrometer, which records the metal concentration of the extracted solution.

Those versed in the art will appreciate that many different variations and adaptations of the present invention fall within the scope of the claims to be presented below.

I claim:

1. A reaction chamber comprising a cylindrical vessel having at a first end, at least one inlet or outlet tube or lead-through fitted with a valve for a liquid or gaseous component, said cylindrical vessel having a second, open end, the reaction chamber further comprising a plunger in sealing relationship with an inner wall of said cylindrical vessel and adapted to perform a reciprocating movement within the cylindrical vessel in axial direction through the open end, said plunger having at least one channel, in substantially axial direction, and fitted with a valve or connected to a tube fitted with a valve.

2. The reaction chamber according to claim 1, wherein said inlet or outlet tube is connected to a multi-channel valve adapted to introduce a sample and at least one reagent successively into the reaction chamber.

3. The reaction chamber according to claim 1, wherein said plunger has a plurality of channels, in substantially axial direction, all fitted with a valve or connected to a tube fitted with a valve.

4. The reaction chamber according to claim 1, wherein said first end of the vessel is fitted with a plurality of tubes or lead-throughs fitted with valves.

5. The reaction chamber according to claim 1, further comprising a drive mechanism operatively connected to said plunger and a control unit for the control of said drive mechanism and said valve.

6. The reaction chamber according to claim 5, wherein said control unit also comprises a programmable processor for the control of said drive mechanism and said valve.

7. A quantitative assay method for the determination of an element generating a gas or a gaseous hydride, comprising
   (i) introducing a sample containing the element, sodium borohydride and an acid into a reaction chamber;
   (ii) reacting said element, sodium borohydride and acid to evolve a gas mixture;
   (iii) displacing said gas mixture into a plasma spectrometer for the element to be quantitatively assayed,
   wherein the reaction is performed in the reaction chamber according to claim 1, into which the sample, sodium borohydride and acid are introduced by aspiration or pumping by driving the plunger outwards in the vessel, and from which reaction chamber the gas mixture evolved in the reaction is displaced by driving the plunger inwards in the vessel, and from which reaction chamber liquid reaction products are finally removed by continuing the inward movement of the plunger.

8. The method according to claim 7, wherein said sample, sodium borohydride and acid are introduced simultaneously into the reaction chamber through the channels in the plunger, the gas mixture evolved in the reaction is displaced through said tube, and by finally removing liquid waste through said channel.

9. The method according to claim 7, wherein movement of the plunger and the position of said valve are controlled by means or a programmable processor.

10. The method according to claim 7, wherein said element is a member of the group consisting of bismuth, germanium, arsenic, selenium, antimony, lead, tin, tellurium and mercury.

* * * * *